United States Patent
Killcommons

(10) Patent No.: US 7,028,182 B1
(45) Date of Patent: Apr. 11, 2006

(54) SECURE NETWORK SYSTEM AND METHOD FOR TRANSFER OF MEDICAL INFORMATION

(75) Inventor: Peter M. Killcommons, San Francisco, CA (US)

(73) Assignee: Nexsys Electronics, Inc., San Francisco, CA (US)

(*) Notice: Subject to any disclaimer, the term of this patent is extended or adjusted under 35 U.S.C. 154(b) by 0 days.

(21) Appl. No.: 09/491,459

(22) Filed: Jan. 26, 2000

Related U.S. Application Data

(60) Provisional application No. 60/120,823, filed on Feb. 19, 1999.

(51) Int. Cl.
*H04L 9/00* (2006.01)
*G06F 17/30* (2006.01)
*G06F 17/60* (2006.01)

(52) U.S. Cl. .............. 713/161; 713/153; 713/182; 713/201; 707/1; 707/3; 707/10; 707/100; 707/104.1; 709/203; 709/217; 709/229; 709/249; 380/277; 705/2; 705/3

(58) Field of Classification Search ............ 713/153, 713/154, 161, 182, 201; 705/2, 3; 707/1, 707/3, 10, 100, 104; 380/277; 709/203, 217, 709/229, 245, 249, 200, 201, 231; 370/474, 370/476, 394, 470; 714/748, 749

See application file for complete search history.

(56) References Cited

U.S. PATENT DOCUMENTS

| | | | | |
|---|---|---|---|---|
| 4,677,588 A | * | 6/1987 | Benjamin et al. | 709/228 |
| 4,712,214 A | * | 12/1987 | Meltzer et al. | 714/748 |
| 4,862,461 A | * | 8/1989 | Blaner | 714/749 |
| 5,321,520 A | | 6/1994 | Inga et al. | |
| 5,469,353 A | | 11/1995 | Pinsky et al. | |
| 5,581,481 A | * | 12/1996 | Weerackody et al. | 341/50 |
| 5,586,262 A | | 12/1996 | Komatsu et al. | |

(Continued)

FOREIGN PATENT DOCUMENTS

| | | | |
|---|---|---|---|
| WO | WO 98/16893 | | 4/1998 |
| WO | WO 98/24358 | * | 6/1998 |
| WO | WO 00/33231 | | 6/2000 |
| WO | WO 02/39364 A2 | * | 5/2002 |

OTHER PUBLICATIONS

MikroTik, PPTP– Point to Point Tunel Protocol.*
Comer, Internetworking with TCP/IP: VPN (Virtual Privat Networks), vol. 1.*
Cisco Systems Inc, Cisco Secure PIX Firewall Series, 1998.*
Kohn, Health Management Technology, Apr. 1997, vol. 18, Iss. 5.*
S. Pruna and N.D. Harris, "Black Sea Telediab: Diabetes Computer System with Communication Technology for Black Sea Region," ITAB '97m Proceedings of the IEEE Engineering in Medicine and Biology Society Region 8 International Conference (Cat. No. 97TH8342), Prague, Czech Republic, XP-002139925, pp. 11–13, Sep. 1997.

(Continued)

*Primary Examiner*—Emmanuel L. Moise
(74) *Attorney, Agent, or Firm*—Blakely, Sokoloff, Taylor & Zafman LLP

(57) ABSTRACT

The assembly and communication of medical information from a variety of modalities to remote stations through a public network is provided for by the combined use of a transmitter and disassembly structure. The transmitter includes an assembly unit for gathering data into packets and a processing unit to provide security for transfer. The disassembly structure reconfigures the data for relay to a receiving station. Mechanisms are provided for conserving the transfer time from transmitter to disassembly structure.

24 Claims, 7 Drawing Sheets

U.S. PATENT DOCUMENTS

| | | | |
|---|---|---|---|
| 5,668,998 A | | 9/1997 | Mason et al. |
| 5,715,823 A | * | 2/1998 | Wood et al. ............... 600/437 |
| 5,740,428 A | | 4/1998 | Mortimore et al. |
| 5,835,726 A | * | 11/1998 | Shwed et al. ............... 709/229 |
| 5,867,821 A | | 2/1999 | Ballantyne et al. |
| 5,898,784 A | * | 4/1999 | Kirby et al. ............... 713/153 |
| 5,924,074 A | | 7/1999 | Evans |
| 5,950,207 A | | 9/1999 | Mortimore et al. |
| 5,986,662 A | | 11/1999 | Argiro et al. |
| 5,987,519 A | * | 11/1999 | Peifer et al. ............... 709/230 |
| 5,988,852 A | | 11/1999 | Nakanishi |
| 6,003,089 A | * | 12/1999 | Shaffer et al. ............. 709/233 |
| 6,154,839 A | * | 11/2000 | Arrow et al. ............... 713/154 |
| 6,272,469 B1 | * | 8/2001 | Koritzinsky et al. ........... 705/2 |
| 6,369,812 B1 | * | 4/2002 | Iyriboz et al. ............. 345/419 |
| 6,412,017 B1 | * | 6/2002 | Straube et al. ............. 709/313 |

OTHER PUBLICATIONS

Rahim S. Pira and John A. Robinson, "Supporting Asynchronous Telemedicine: Multimedia Mail v. The World Wide Web v. Replicated Databases," Conference Proceedings IEEE Canadian Conference on Electrical and Computer Engineering, Waterloo, Ontario, Canada, XP-002139926, pp. 341-344, May 1998.

G. Haufe and Jakob S. Northrup, "PACS at Work: A Multimedia E-Mail Tool for the Integration of Images, Voice, and Dynamic Annotation," Proceedings of the International Symposium On Computer and Communications Systems for Image Guided Diagnosis and Therapy, Proceedings of CAR '96: Computer Assisted Radiology—10th International Symposium, Paris, France, XP-000914152, pp. 417-420, Jun. 1996.

Ruth E. Dayhoff, et al., "Mechanisms for Exchange of Image Data to Support Distant Medical Consultation," Proceedings of Seventeenth Annual Symposium on Computer Applications in Medical Care, Washington, D.C., USA, XP-000914151, pp. 808-812, Oct. 30-Nov. 3, 1993.

Maria Grazia Bitti, MD., et al., "A WWW-Based Distributed System for Medical Data Analysis and 3D Reconstruction," Computer Assisted Radiology, Proceedings of the International Symposium, XP-002057164, pp. 345-350, Jun. 1, 1996.

James H. Thrall and Giles Boland, "Telemedicine in Practice," Seminars in Nuclear Medicine, vol. 28, No. 2, pp. 145-157, Apr. 1998.

W. Dean Bidgood, Jr., MD, MS, et al., "Understanding and Using DICOM, the Data Interchange Standard for Biomedical Imaging," Journal of the American Medical Informatics Association, vol. 4, No. 3, pp. 199-211, May/Jun. 1997.

"Medweb Plug-in," Medweb Distributed Medicine, Medweb, 1996.

"Medweb's Teleradiology Plug-in, Software Manual for Use with Windows 95," Medweb Distributed Medicine, Medweb, Apr. 1997.

"Integrated Solutions Catalog," Medweb Distributed Telemedicine, Medweb, 1995.

Computer Dictionary, Third Edition, Microsoft Press, p. 268, 1997.

Tom Abate, "Entrepreneurs Discover Internet," San Francisco Examiner, Business Section, entire article, May 29, 1994.

"Medweb Plugin Turns Netscape Browser into a Medical Imaging Workstation; Medweb Radiology Workstation Plugin Saves Hospitals Millions of Dollars," Business Wire, entire article, Dec. 4, 1996.

Tom Abate, "Setting Up Shop on the Internet Entrepreneurs Explore It's Commercial Potential," San Francisco Examiner, Business Section, Jul. 14, 1994.

Donald E. Eastlake III, "Secret Key Establishment for DNS (TKEY RR)," DNSSEC Working Group, Sep. 1998.

R. Atkinson, "IP Authentication Header," Network Working Group RFC 1826, Aug. 1995.

R. Atkinson, "IP Encapsulating Security Payload (ESP)," Network Working Group RFC 1827, Aug. 1995.

D. Eastlake III and C. Kaufman, "Domain Name System Security Extensions," Network Working Group RFC 2065, Jan. 1997.

D. Eastlake III, "Secure Domain Name System Dynamic Update," Network Working Group RFC 2137, Apr. 1997.

S. Kent and R. Atkinson, "IP Authentication Header," Network Working Group RFC 2402, Nov. 1998.

S. Kent and R. Atkinson, "IP Encapsulating Security Payload (ESP)," Network Working Group RFC 2406, Nov. 1998.

William Stallings, "Cryptography and Network Security: Principles and Practice, $2^{nd}$ Edition," Chapter 13: IP Security Prentice Hall, 1999.

"Images-on-Call: Teleradiology & Image Distribution Networks," Devices & Services Company, Date Prior to Jan. 26, 2000.

"ACCESS Radiology Corporation Acquires EMED Creating the Preeminent Teleradiology/Image Distribution Provider", Access Radiology Corporation Press Release, Nov. 23, 1998.

"PhysiTel: Telemedicine for the real world!", Oct. 21, 1998. http://www.physitel.com/software.shtml.

"PhysiTel: Telemedicine for the real world: What's Required to Make My PC A Telemedicine System?," Oct. 21, 1998, http://www.physitel.com/need.shtml.

"PhysiTel to Develop Innovative Teledentistry Software for UCLA School of Dentistry," PhysiTel press release, Aug. 17, 1998. http://www.physitel.com/press.shtml.

"Open Systems Interconnection (OSI) Model," pp. 678-683, Date Prior to Jan. 26, 2000.

"Simple Mail Transfer Protocol (SMTP)," pp. 795-796, Date Prior to Jan. 26, 2000.

"INPHACT: The Radiology Solutions Company," Brochure, Date Prior to Jan. 26, 2000.

"On Display: RSNA Guide to Radiologic Technology 1998-1999," pp. 1-206, Radiological Society of North America, 1998.

* cited by examiner

| AE TITLE Receiving Station 30 | COMPRESS 38 | ENCRYPT 40 | ALIAS AE TITLE Disassembly St 32 | IP ADDRESS Disassembly St 34 | PORT# Disassembly St 36 |
|---|---|---|---|---|---|
| WS-SiteB | 3:1 | DNSSec 3des | Disasem 3 | 1.2.3.7 | 104 |
| Archiv-SiteB | 3:1 | IPSec 3 | Disasem 3 | 1.2.3.7 | 104 |
| WS-SiteC | 2:1 | IPSec 3 | Disasem 4 | 1.24.7 | 104 |

SECURE NETWORK SYSTEM AND METHOD FOR TRANSFER OF MEDICAL INFORMATION

RELATED APPLICATION

This application is related to and hereby claims the priority benefit of a provisional application entitled "Secure Network System and Method For Transfer of Medical Information" filed Feb. 19, 1999, and assigned Application No. 60/120,823.

NOTICE OF COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates generally to the transfer of medical information through a public network, and more particularly to a network system for secure communication of medical information across a virtual private network.

BACKGROUND

In many fields (e.g., medicine, manufacturing, veterinary science, scientific research, etc.), it is often necessary to examine a subject and communicate the results of the examination to a remote place. Such information exchanges are especially desirable in the medical arena where it is often useful for medical practitioners to communicate medical information, such as patient test results, e.g., radiology studies or cardiac studies, to other practitioners located in remote places. Telemedicine facilitates this exchange of information. Telemedicine is generally the electronic transmission of medical data from one location to another for purposes of interpretation and consultation. Telemedicine is gaining interest in the medical community, in part due to an increasing shift in health care delivery from hospitals to physician offices, extended care facilities, ambulatory treatment centers and patients' homes.

The medical information communicated by telemedicine systems may be derived from a variety of different medical modalities. Such modalities may include sophisticated radiology equipment grouped as small matrix size and large matrix size instruments. Small matrix size systems include equipment for magnetic resonance imaging (MRI), computed tomography (CT), ultrasonography (US), nuclear medicine (NM) and digital fluorography. Large matrix size systems include equipment for computer radiography (CR) and digitized radiography (DR). Other data image acquisition equipment may be used for radiofluoroscopy, angiography, such as x-ray angiography and heart scanning. Still other equipment of great usefulness in acquiring medical information includes secondary capture devices for video, endoscopy, microscopy, and photography, such as digital cameras, scanners, electrocardiogram (ECG) machines, and the like.

The resulting medical information may take numerous forms, including text, images and video, or variations thereof, such as image overlay data, measurements, coordinates, etc. Information may also be in the form of time-dependent data including sound, such as audio dictation, and waveform data. The data may be static representations of time-dependent forms, such as curves. Thus, it is advantageous for telemedicine systems that may need to transfer the data and/or information to be flexible, so as to accommodate this variety of information/data from multiple modalities.

Typically a medical study on a patient results in a very large data file which may include a combination of data forms. For example, an MRI study on a patient may include text and about 100 images, each of which may be 300 to 500 Kb in size, loading to a study of 50 to 80 Mb total of data. This large amount of data presents a particular problem for the rapid sharing of medical information. Time is often of the essence during healthcare decision making. For example, an attending practitioner may need to obtain immediate advice on caring for a patient from a remotely located specialist. Therefore, it is critical that telemedicine systems transfer large data files in a timely fashion.

It is also important that telemedicine systems provide for the transfer of such large amounts of data without data loss. Some medical industry standards require that medical information transferred by telemedicine systems maintain sufficient detail for accurate interpretation by the practitioner. Multi-specialty DICOM Standards describe acceptable parameters to manage delivery of multimedia medical information. The DICOM Standards were originally published by an ACR-NEMA committee sponsored by the American College of Radiology and the National Electrical Manufacturers Association as Digital Imaging and Communications in Medicine (DICOM), NEMA Publications PS 3.1–PS3.12, by The National Electrical Manufacturers Association, Rosslyn, Va., 1992, 1993, 1994, 1995. These DICOM Standards define the form and flow of electronic messages that convey images and related information between computers through TCP/IP. Therefore, it is desirable for medical information transfer systems to acquire and transmit complex data, such as radiology images, in a manner that complies with the DICOM Standards. See, e.g., Bidgood, et al., "Understanding and Using DICOM, the Data Interchange Standard for Biomedical Imaging," J. Am. Med. Informatics Assoc., 4:3, 199–212, May–June, 1997. The transferred information should be presented in the context and form that is most helpful for practitioners to make sound health and wellness decisions.

The medical profession is also under a strict duty to protect the confidentiality of patients' medical records. Thus, protection of medical data/information in telemedicine is of paramount importance. Most telemedicine systems include some form of security measures such as the use of passwords. Password identification determines whether a user is authorized to gain access to a system. However, passwords are insufficient mechanisms to maintain patient confidentiality from intruders who gain knowledge of a user's password to log onto a system and "man in the middle" attacks on the Internet.

For secure and fully private long distance communications, point-to-point connections between sites have been employed. Private networks, such as wide area networks (WAN's), are typical. Unfortunately, these systems are inflexible and involve prohibitive costs. Large telemedicine networks that span long distances, e.g. across continents, become too costly for current conventional private WAN architecture. Since all sites must be hardwired, the addition of new sites to the network is inconvenient. A medical enterprise must install and support terminal equipment and software for each WAN site. Furthermore, the volume of information designated to travel over the network may overload the system. For example, rural medical sites may only have access to poorly maintained telephone lines that are an inadequate medium for transmission of medical data.

Public networks provide a flexible and inexpensive option for long distance internetworking. Each of the remote sites in a medical network need only be connected to a local Internet provider. Adding new connections is simple and inexpensive. Once connected to a local Internet provider, a site can quickly connect to any destination around the world allowing a practitioner at one location to interpret medical test results and consult with another practitioner located elsewhere.

There are few places of the globe that the Internet can not reach. Medical information transfer systems that employ the Internet may allow for remote locations, such as third world countries that do not have an attending specialist, to access needed medical expertise. Furthermore, emergency care may be provided where a practitioner is temporarily away, e.g., at home or on vacation. See, e.g., Thrall J H, Boland G., "Telemedicine in practice", Seminars in Nuclear Medicine 28(2):145–57, April 1998.

However, traditionally medical networks have avoided transfer of information over the Internet, in part, because of security constraints. The Internet includes public segments, where the same infrastructure is shared by potential competitors, hackers, and the like. Such public networks expose the medical enterprise to at least the following two dangers: (1) unauthorized Internet access into the medical network and (2) eavesdropping on and tampering with a communication as it passes through the Internet.

A virtual private network (VPN) may use both private and public network segments or entirely use public segments e.g., the Internet, to link resources together into a single network. Encryption technology employed at connections between private and public networks can be used to protect the data transferred between such networks as if the connection between them was entirely private. Such use of encryption in virtual private networks provides some security measures for the transfer of sensitive information.

Another problem with the use of the Internet is that the heavy traffic flowing over public connections may lead to delay problems in the transfer of the large amounts of data. Most Internet systems are not structured to allow for quick transfer of the volume of data files that are typical of medical information. Transfer efficiency depends on, inter alia, characteristics of the network segments that the packets must traverse, congestion on those segments and efficiency of the dispatcher. High delay environments include satellite connections, national links and international links.

Furthermore, where more data is attempting to flow between two points than a public system can handle, the data packets are simply thrown away by overloaded routers. Lost packets must be resent by the dispatcher, typically in a manner that is time consuming and renders the telemedicine system unusable. Transfer systems used to transmit data compliant with DICOM standards are usually designed to abort incomplete file transmissions and to restart the transfer from the beginning of the file, rather than just resending the failed packets. Telemedicine systems that employ mechanisms used to compensate for latency and loss of data in transfer are of great interest.

Moreover, typical transfer systems that are used to transmit DICOM compliant data are not appropriately configured to transfer data over the Internet. These systems have IP addresses that are suitable to destinations within a local area network. However, often these same IP addresses are unacceptable for the routers on the Internet. This factor, compounded with an overall shortage of routable IP addresses available for transfer systems in general, makes transfer of medical data directly from medical modalities across the Internet complicated.

Thus, in light of the shortcomings of the various currently available systems, there is still a need for secure medical transfer systems that allow for transfers of large amounts of data in a timely and efficient manner. In particular, there is a desire for telemedicine systems that use an encrypted and reliable Internet protocol to create a protected communication pipeline. Moreover, there is a need for systems that can move DICOM or other medical data between hosts by providing routable IP addresses.

SUMMARY OF THE INVENTION

In one embodiment, a transmitter is provided for sending medical information into a network. At least a portion of the network includes secured public channels to create a virtual private network. The transmitter includes a data interface for acquiring medical data and a network interface for transferring the medical data into the network for receipt at a disassembly structure. An assembly unit may be used to gather the medical data acquired by the transmitter and to form packets that include such data. In some cases, the transmitter includes a remapping unit to attach an address to the packets for identifying the disassembly structure that is to receive the packets as well as receiving station(s) for the medical data's ultimate destination(s). In one embodiment the remapping unit attaches alias application entity titles (alias AE titles) to the packets. The remapping unit may also serve as a network address translator (NAT) to attach routable IP addresses to the packets.

Often, the transmitter will include a processing unit configured to encrypt the medical information across protocol layers prior to the packets being sent into the network, thus providing confidentiality during the data transfer. Internet Procotol Security (IPSec) Standards may be employed by the processing unit for providing these secure data transfers. In other configurations, the processing unit may be configured to authenticate and/or provide key management to the packets across protocol layers. The transmitter may further include a firewall. One such firewall has a network port at the data interface and another network port at the network interface.

The transmitter may employ mechanisms for conserving the time it takes for transfer of a medical study to the disassembly structure. In one such mechanism, the assembly unit compiles large amounts, e.g., between 0.1 megabyte and 5.0 megabytes, of data into packets. A confirmation unit in the transmitter may receive acknowledgement of a completed packet transfer within a threshold time. In some cases, the threshold time may be set at 1 to 500,000 msec. Then, in some embodiments, only the packets to which no acknowledgement is received within the threshold time are resent.

The medical information transferred by the transmitter may be text, image, overlay, 3-D volume, waveform, curve, video or sound data, or any combination thereof. The data entering the transmitter is preferably in compliance with DICOM Standards and/or HL7 Standards. In some cases, the transmitter changes the form of the data to not conform to DICOM Standards and the disassembly structure reconfigures the data to adhere again to DICOM Standards.

Another embodiment provides a medical virtual private network system that includes at least one medical modality to generate medical data. This data may be sent to an information transmitter through an associated data interface. One or more disassembly structures communicatively coupled to the transmitter through the network may receive the data in the form of packets transmitted by the transmitter. Such disassembly structures decrypt the data packets and relay the data to at least one receiving station. The disassembly structure optionally is a transmitter, including features of both the disassembly structure to receive data and a transmitter for gathering data from modalities and sending the data over the network.

Still other embodiments may provide a computer readable medium having stored therein a plurality of sequences of instructions, which when executed by a processor, cause the processor to perform certain steps. Among these steps may be included the steps of assembling medical data into packets; remapping IP addresses or alias AE titles to the packets for identifying a disassembly structure; encrypting the packets across protocol layers; and/or sending the packets into a pubic network for receipt at the disassembly structure. Of course, other embodiments may provide only the instructions themselves or methods of performing these steps.

Other features and advantages of these and other embodiments are discussed in detail below.

BRIEF DESCRIPTION OF THE DRAWINGS

The present invention is illustrated by way of example, and not limitation, in the figures of the accompanying drawings in which:

FIG. 3 is an example of a table of a relational database that may be used by the remapping unit of a transmitter in accordance with the methods described below.

FIGS. 4A–4B illustrate the fields of a secured medical data packet in accordance with the teachings presented herein, wherein FIG. 4A shows a packet constructed in accordance with IPSec Standards using AH protocol and FIG. 4B shows a packet constructed in accordance with IPSec Standards using ESP protocol.

FIGS. 5A–5B are a flow diagram of methods of resending incomplete transmissions, wherein FIG. 5A shows a process to reduce transfer time for transmission of a medical data file in accordance with the present methods and FIG. 5B shows a prior art process of resending an entire data file.

DETAILED DESCRIPTION

The Medical Network System and Method for Transfer of Information described below is configured to provide reliable, secure and flexible communication of medical information including medical images and clinical data to remote facilities and users. The system utilizes a transmitter that includes a variety of safeguard services to provide this protected network environment across the Internet. The transmitter is further configured to permit easy additions of new sites to the network. By incorporating efficient packet assembling and receiver acknowledgment techniques into the system, bulky medical information may be rapidly transferred to any desired destination.

Figure 1:
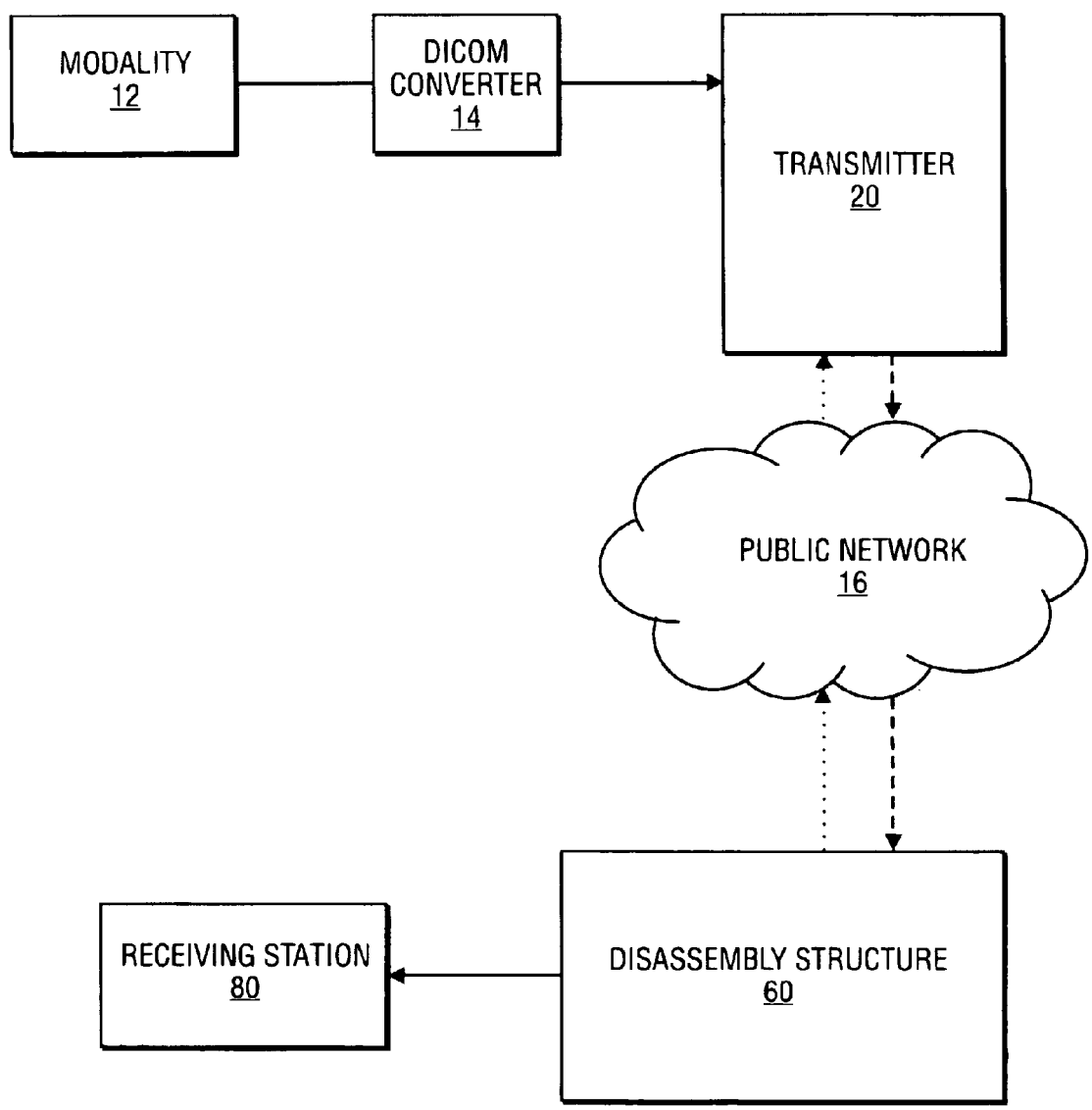
FIG. 1 illustrates one embodiment of a medical virtual private network configured in accordance with the teachings presented herein.

FIG. 1 illustrates an exemplary secure network system 10 configured in accordance with one embodiment of the present invention. A modality 12 is coupled to a transmitter 20 through a DICOM converter 14. A disassembly structure 60 receives communication from the transmitter 20 across a public network 16. The disassembly structure 60 may send the medical information to receiving station 80, which station may optionally display, manipulate, store and/or print data captured/provided by modality 12. The disassembly structure 60 may also transmit an acknowledgement of receipt of such medical information to the transmitter 20. It should be noted that the scope of the present invention anticipates any number of modalities, transmitters, disassembly structures and workstations configured in accordance herewith and arranged in various fashions.

The modality 12 may be any type of device that generates data or data signals related to the examination of a subject. The subject is preferably a human being or an animal (or a portion of either thereof), but may also be an inanimate object that is being inspected. The modality may perform the direct examination of the subject, where the modality includes a detection component. Alternatively, the modality 12 may create data or signals from a user's input, where the modality has an input component such as a keyboard, mouse, microphone, etc.

Although the modality 12 may pertain to the examination of a subject in any number of fields, such as manufacturing, veterinary science, scientific research, etc., the modality is preferably a medical device to retrieve data related to a subject's physical condition. Medical modalities used in radiology include data acquisition equipment for magnetic resonance imaging (MRI), computed tomography (CT), ultrasound (US), nuclear medicine (NM) and digitized radiography (DR), computer radiography (CR) and digital fluorography. Other modalities include photographic devices such as high resolution digital cameras; sound capture interfaces such as verbal dictation interfaces, Sound Blaster™ interfaces, and the like; video capture interfaces such as Snappy® brand parallel port video capture devices; flatbed scanners and especially Twain compliant acquisition devices such as Visioneer Paperport®. Still other modalities are for angiography, radiography, endoscopy, microscopy, physical exams and waveform devices to collect EEG and/or ECG data, such as from Hewlett Packard Corporation of Palo Alto, Calif. and American Medical Devices Corporation of Lowell, Mass. In addition, the present invention anticipates other modalities and all of the aforementioned modalities are by way of example, and are not intended to limit the choices that are or may become available in the art. The data may be captured by such devices with assistance of specialized software, such as the plugin or ActiveX control technologies, as described, for example, in copending patent application, U.S. Ser. No. 09/199,611, filed Nov. 25, 1998, entitled MEDICAL NETWORK SYSTEM AND METHOD FOR TRANSFER OF INFORMATION.

The data that is captured by the modality 12 and transferred by a secure network system configured in accordance with the present teachings may take numerous forms. Some common formats include text, images, video, sound, such as audio dictation, waveform, curves, and/or combinations or variations thereof. Medical data of this sort may be grouped into various types. Where the data entering the transmitter are medical data, the data maybe formatted to be in compliance with several medical standards, for example DICOM and HL7 Standards. Clinical data is information acquired by a medical modality during the examination of a patient and relates to the patient's physical health. Examples of clinical data may include radiology images, camera photographs, sound recordings, and the like. Parameter data is another type of data representing criteria surrounding the acquisition of clinical data. Parameter data includes the settings of the medical modality acquiring the clinical data, relationships of multiple sets of data such as overlay data, timing of the data acquisition, measurements, coordinates, and the like. The parameter data includes some of the information required by the DICOM Standards for stored and transferred medical files. Other medical data may include 3-D volume data; series data for all clinical data in a medical series, e.g., coronal slices vs. axial slices in a CT exam or echoes as T1 slices vs. T2 slices in an MRI exam; annotation data for notes made by a practitioner, usually relating t the clinical data; and background data such as patient history and/or physical examination information.

DICOM Standards require that transferred data have application entity titles (AE titles) to designate the applications and stations which are to ultimately receive the data. In addition to AE titles, the DICOM Standards also require that transmitted data include IP addresses and a port numbers to identify the medical data's final destinations. The modality generating the data may attach individual AE titles for every receiving station to acquire the data, as well as IP addresses and port numbers.

In a preferred embodiment of the present invention, the use of an AE title is extended to define the disassembly structure for which the data is intended and optionally other useful information such as directions on the compression and encryption associated with the transferred medical data. This additional information is captured within an alias AE title that is attached to the data. The alias AE title may be recognized by all transmitters and disassembly structures located in a particular medical network. Whereas a normal AE title is used to identify a receiving station by devices which connect directly to the station, an alias AE title is used for data transferred through an intermediary disassembly structure, according to the present invention. For example, local devices, such as within a LAN, may use an AE title to direct information straight to the receiving station, but a device connecting to the same station through a transmitter and disassembly structure gateway may use an alias AE title. Often, a particular alias AE title is designated by the disassembly structure associated with each receiving station and any transmitter sending information to that disassembly structure must use its alias AE title.

As shown in FIG. 1, the dicom converter 14 receives data from modality 12 and conveys the data to transmitter 20 where it may be processed and sent to disassembly structures 60. Dicom converter 14 is an optional component to the secure network system 10 that converts the raw data into DICOM compliant data. Dicom converter 14 may be a stand-alone device, such as Dicomizer™ (by Nexsys Electronics, dba. Medweb Inc. located in San Francisco, Calif.) or alternatively, may be an integral part of a computer system for controlling the operations of the modality. In the latter case, the modality is equipped to output data conformant with DICOM Standards.

The transmitter 20 in secure network system 10 is any device, such as an IP host, computer or server (and may include a firewall or router) that receives medical data and transmits the data through a network. Preferably at least a portion of the network is a public network, e.g., a virtual private network or the Internet. The transmitter may be a server as described in copending patent application, U.S. Ser. No. 09/199,611, the contents of which is herein incorporated by reference in its entirety, and further includes the transmitter components to be described below.

Figure 2:
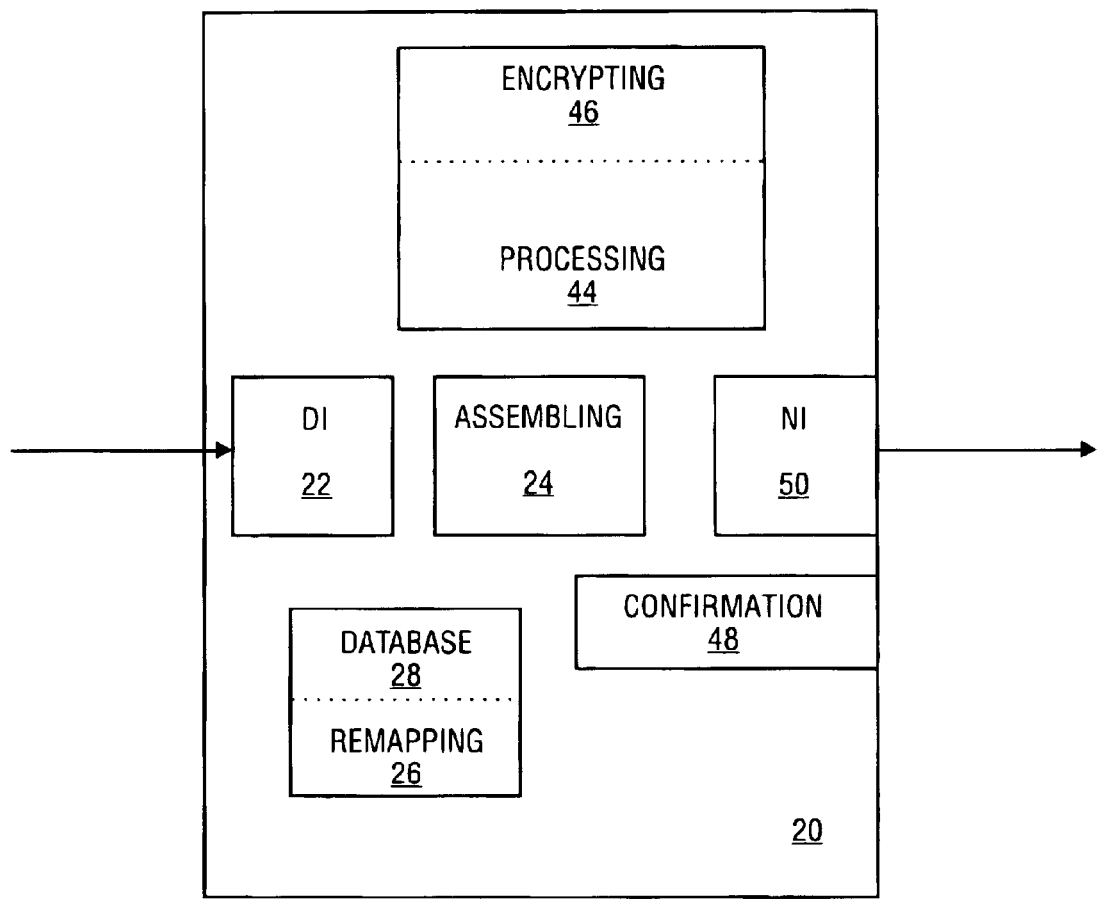
FIG. 2 is a block diagram of one embodiment of a transmitter configured in accordance with the teachings presented herein.

As shown in FIG. 2, transmitter 20 has components for handling data in various ways. These components include a data interface (DI) 22 to receive newly acquired data, an assembly unit 24 for gathering together information, a remapping unit 26 for attaching addresses to the data, a processing unit 44 for manipulating the data and a network interface 50 for sending the information so processed. Upon review of this specification, it will be appreciated by those skilled in the art that the components of transmitter 20 may be connected in various ways in addition to those described below.

In one embodiment, modality 12 may communicate with the data interface 22 through an Ethernet connection (i.e., the data interface 22 may be an Ethernet port). However, other communication schemes are suitable for transfer of data from modality 12 to transmitter 20, such as serial interfaces, parallel interfaces, RS422 and/or RS432 interfaces, Livewire interfaces, IEEE-1394 serial busses, Appletalk busses, ATM busses and/or networks, token ring and/or other local area networks, universal serial buses, PCI buses and wireless (.e.g., infrared) connections, and the like.

Now referring in more detail to the transmitter components shown in FIG. 2, an assembly unit 24 may be coupled to the data interface 22 and gathers newly received medical data to form packets. The assembly unit 24 breaks messages into packets, e.g., as according to the TCP protocol.

In a preferred embodiment, the assembly unit groups an amount of medical data into each packet that is larger than what is typically assembled into a packet traveling across the Internet. Generally, Internet procedures, e.g. TCP/IP, assemble about 750 bytes to 1 kilobyte of data into a single packet. In contrast, according to this embodiment, assembly unit 24 collects greater than 1 kilobyte of data and usually between about 0.10 megabytes to 5.0 megabytes and more usually about 1 megabyte of data. In one example, a MRI study is 80 megabytes. By current Internet procedures, each packet of data may include 1 kilobyte of data and take 300 msec to travel from a server across the Internet and to its destination. Consequently, the entire study takes at least 400 minutes to be transferred, assuming that every packet arrives to its destination the first time that they are sent. By comparison, in one example of the present invention, 1 megabyte of medical data of the same 80 megabytes MRI study is assembled into each packet. As a result, the number of packets is reduced by 1000 fold.

These larger packet sizes shorten transfer times by reducing the number of packets per study that must travel across often lengthy distances to reach their destination. For example, each packet sent via satellite transmissions may need to voyage about 50,000 miles. Moreover, fewer acknowledgment-of-receipts are needed to be sent for each packet by the disassembly structure. The result is significant savings in the time it takes for a medical study to be communicated to a disassembly structure.

In another embodiment, the assembly unit is configured to gather the medical data into very small packet of message transfer unit (MTU) sizes. For example, each packet may be 50 bytes to 500 bytes, and usually 50 to 200 bytes, and more typically 50 to 100 bytes. These very small MTU's are particularly useful in transmitting data across congested networks. In congested Internet environments, decreasing the size of a MTU to less than 1.0 kilobyte may effect successful transport of packets through congested routers, where the routers tend to lose larger packets.

Transmitter 20 is further equipped with a remapping unit 26 for assigning destination addresses to the data. The remapping unit 26 may be coupled to the assembly unit. The attached address may be several different formats, such as alias AE title, IP address, etc.

In one embodiment, the remapping unit reads the header text that identifies the receiving stations for the data, determines the disassembly structure for that receiving station and attaches the address for the disassembly structure to the packet.

In another embodiment, the destination address is an alias AE title. In this configuration, remapping unit 26 reads the AE titles to the receiving stations that are to be the data's ultimate destinations. As shown in the table in FIG. 3, a relational database 28, usually in the form of a table, is used to cross-reference the AE titles 30, to identify the disassembly structures that are associated with each of the data's intended receiving stations. The disassembly structures' alias AE titles 32 are then determined and attached to the data packets.

In still a further embodiment, the destination address attached by remapping unit 26 is a routable IP address 34 to the disassembly structure. The remapping unit 26 acts as a Network Address Translation (NAT) component. The term "routable IP address" refers to an IP address that designates a disassembly structure or transmitter and is acceptable by routers to direct the packets across the Internet. The routable IP address is usually globally registered. The term "private IP address" refers to the IP address for a receiving station associated with a disassembly structure or the IP address for a modality that is the source for data transferred by a transmitter. Usually the private IP address is not routable across the Internet.

Whereas DICOM Standards require that each destination device be directly addressable, the remapping unit 26 may allow all of the receiving stations to share the same routable IP address to the disassembly structure. After the disassembly structure receives the data packets, the disassembly structure delivers the data to the appropriate receiving station. Similarly, the private IP address for each modality source of the data may be substituted for a routable IP address to the transmitter. Thus, replies received by the transmitter may have the source modality's private IP address restored and the replies are directed to the appropriate source. In this manner, one may transfer DICOM compliant data across the Internet without having to register numerous IP addresses.

Often the remapping unit 26 performs both AE title remapping and NAT. The database 28 may list the alias AE titles 32, routable IP addresses 34 and port numbers 36 for each disassembly structure. An unlimited number of AE titles and IP addresses may be stored in the database, and usually between 50 and 100. The IP addresses and port numbers, and optionally the AE titles, for each appropriate disassembly structure is attached to the data packets. In an exemplary embodiment, the database also retains information on the compression ratios 38 and types of security, such as encryption 40, which should be used to transmit the data. Thus, in one embodiment, after remapping, the packets include the data as well as the following: a disassembly structure's routable IP address and port number; an alias AE title to the disassembly structure; and a receiving station's AE title, private IP address and port number.

In one case, the packets leaving the transmitter are no longer compliant with DICOM Standards. For example, alias AE titles may be provided rather than the DICOM specified AE titles. The packets may become DICOM compliant again by the disassembly structure restoring appropriate DICOM information, e.g. AE titles, to the data prior to transferring the data to the receiving station.

In an alternative embodiment, the remapping unit examines the content of the data for information and uses this information to determine which receiving station and disassembly structure is to receive the data. The remapping unit then attaches the appropriate address to the packet. One example of content-based information is the type of medical data in each packet, wherein the receiving station is designated to accept a specific type of data. In one example, the data is a mammogram and the data is automatically forwarded to a remote mammogram-screening center. A processing unit 44 in the transmitter 20 provides a mechanism to process the data packets prior to data transmission via various manipulation components, e.g., encryption component 46. For example, processing unit 44 may be a general-purpose processor that transfers data to and from the manipulation components. Alternatively, processing unit 44 may be a processor configured to execute instructions defined by manipulation components (e.g., where encryption component 46 is a computer program). Commonly, the processing unit 44 is coupled to the assembly unit or remapping unit.

The encryption of data by encryption component 46 provides for secure transmission of data to the disassembly structure, usually by scrambling the message, whereas the disassembly structure may be used to decrypt, or unscramble, the data. Some types of encryption include Internet Protocol Security (IPSec) for providing encryption of all traffic between two security gateways, e.g. the transmitter 20 and the disassembly structure 60, secure socket layer (SSL) and transport layer security (TLS) for securing Web browser communications and pretty good privacy (PGP) for protecting e-mail communications.

In some cases the processing unit 44 is also configured to authenticate the packets. Authentication validates the sender of a packet, prevents undetected modification to a packet's content in transit and stops address spoofing attacks by protecting IP addresses, port numbers and AE title fields. Authentication may be through use of a digital signature to identify the author of a message.

In other embodiments, the transmitter 20 is further configured to provide key management to the packets. The present medical network requires that only the transmitter 20 and disassembly structure 60 be assigned keys. Thus, the present scheme allows for fewer keys to be distributed, compared to other systems that require all receiving stations to have keys.

Either manual or automated key management may be employed, and usually an automated system is used. In preferred embodiments, an Oakley Key Determination Protocol is employed with Internet Security Association and Key Management Protocol (ISAKMP).

Other security measures may be taken to provide non-repudiation by providing cryptographic receipts. In this manner, an author of a message may not falsely deny sending the information.

Such security services, i.e., encryption, authentication and key management, preferably conform to IPSec Standards, as developed by William Stallings, the Internet Engineering Task Force to provide end-to-end security for packets. See, e.g., Cryptography and Network Security, $2^{nd}$ ed., Prentice Hall, NJ, pgs. 399–440, 1999. IPSec provides security services at the IP layer, i.e., optional in IPv4 and mandatory in IPv6, and below the transport layer, e.g., TCP, UDP, so it is transparent to applications and end users.

The security benefits of IPSec are numerous. IPSec provides for connectionless integrity to verify that messages are not modified in transit by using an authentication data field, data origin authentication, confidentiality and limited traffic flow confidentiality. In one embodiment of the present invention with IPSec, replayed packets are rejected by use of a sequence number field to increase a number counter for each packet that is sent to a particular disassembly structure. The disassembly structure verifies that the packet has not yet been received if the number has not yet been accounted for or discards packets with replicated sequence numbers.

The processing unit may attach headers to the packets in accordance with IPSec. Where authentication is provided by the transmitter, the header of a protocol, Authentication Header (AH), is attached to the packet. AH is described in RFC 1826. In one preferred embodiment, both authentication and encryption are provided by a header for the protocol, Encapsulating Security Payload (ESP). ESP is described in RFC 1827. Both RFC 1826 and RFC 1827 are updated in RFC 2402 and RFC 2406 respectively.

The present scheme also anticipates use of either transport mode or tunnel mode for transferring packets across the secure network, and more often tunnel mode is used. On occasions where transport mode is used, the upper-layer protocols are protected. For example, the AH or ESP header is inserted after the original IP header and before the TCP segment. The part of the packet not required for routing is encrypted.

In tunnel mode, the transmitter protects the entire IP packet, such that the entire packet is encrypted and placed inside of another packet with normal routing information. This is done at a level in the kernals of the transmitter between the basic routing and the socket layer code The transmitter treats the security fields as a new outer IP packet that encapsulates the original packet. For example, the AH or ESP may be inserted between the original IP header and a new outer IP header containing sufficient information for routing. In exemplary encapsulated packets shown in FIGS. 4A and 4B, the data packet 100 has an outer packet 102 that contains, an alias AB title (not shown), a routable IP address 104, and port number 106 to the disassembly structure. The inner packet 122 carries the IP address 124, port number 126, and AE title 128 to identify the receiving station, as well as the transport layer header 132, such as TCP, UDP and ICMP, the data 130 that was assembled by the transmitter and a compression header 134. Typically, no intermediate routers along the communication line may examine the inner IP header. These interim machines do not know that the packets they are passing are encrypted.

Figure 4A:
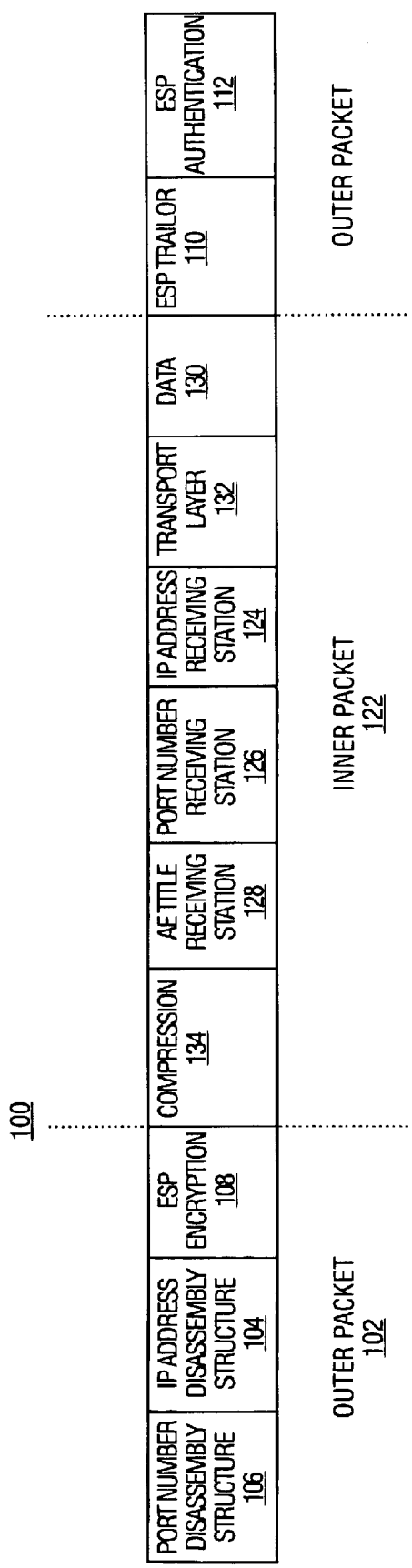
Figure 4B:
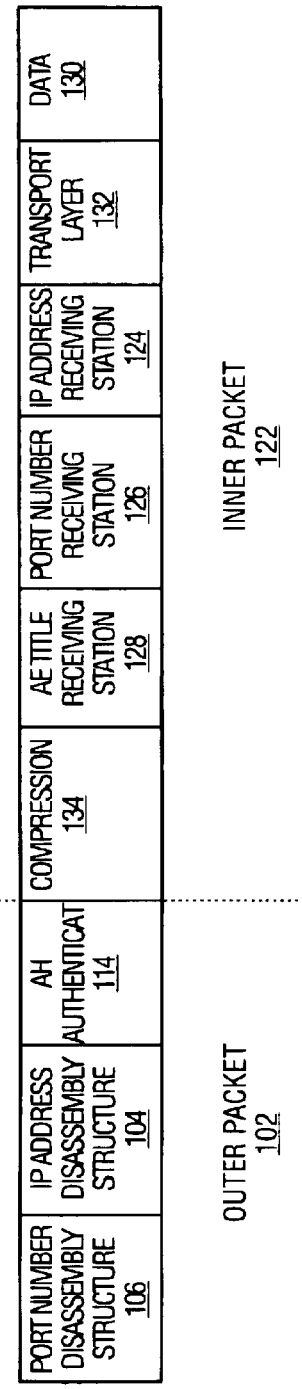

In FIG. 4A, an ESP header 108, ESP authorization header 112 and ESP trailer 110 is also added to the outer packet. The ESP trailer 110 may include padding, pad length and next header fields. In FIG. 4B, an AH header 114 is added to the outer packet instead of the ESP header 108, ESP authorization header 112 and ESP trailer 110.

Transmitter 20 also includes a network interface 50 configured to send the packets into the network connection and to disassembly structure 60 such as with the IP protocol.

The transmitter 20 may further include an acknowledgement unit 48 that is configured to receive acknowledgements that a disassembly structure 60 has received a packet sent by the transmitter. The transmitter 20 may have a predefined threshold of time (as maintained by an internal timer) in which an acknowledgement unit 48 will consider a received acknowledgment as representing a successful transfer of a packet. In preferred embodiments, the threshold time is longer than the threshold time used in typical Internet systems and is generally about 1 to 500,000 msec and more typically 100,000 to 250,000 msec. The chosen threshold time may be set to correspond with the latency in transmission which may depend, inter alia, on the type of transmission pipeline across which the packets travel. For example, where the packets must traverse very long distances, such as via satellite transmissions, the latency may be longer and threshold time is accordingly extended. In addition, where the packets must travel across congested lines, a longer threshold period is used. In this manner, the transmitter 20 avoids considering packets lost in cases where the acknowledgment may take longer to be received.

If acknowledgement unit 48 does not receive an acknowledgement for a packet within the threshold time, the packet is considered lost and the connection between transmitter and disassembly structure breaks. Where a single packet of a series of packets comprising a study is lost, conventional protocols require that connection become reopened and the entire study be resent from the starting packet. Thus, even packets that were initially received by the disassembly structure and for which acknowledgments were successfully sent, are transmitted to the disassembly structure again. This redundancy in transmitted packets wastes precious time in transmitting a medical study.

However, a preferred embodiment of the present invention avoids redundant transmissions of packets by including procedures in which the transmitter 20 only sends those packets for which acknowledgment is not received, rather than sending all packets over again. The present network system adds another level of intelligence that closely links the software components which track file transmission progress, i.e. how much of the file has been transmitted, with the underlying transmission protocol which tracks packet loss and retransmission. As a result, the socket connection may be opened and closed many times over the course of transmitting one file, but the file transmission always makes progress when the connection is up, rather than starting over.

Figure 5A:
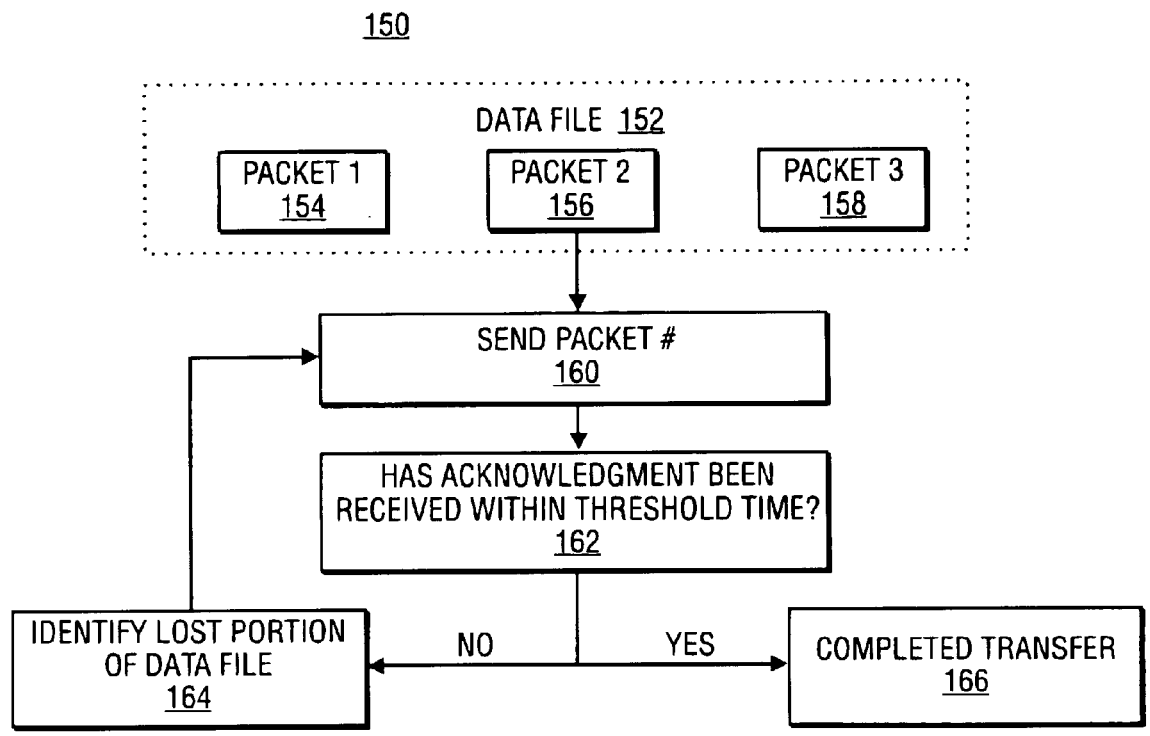
Figure 5B:
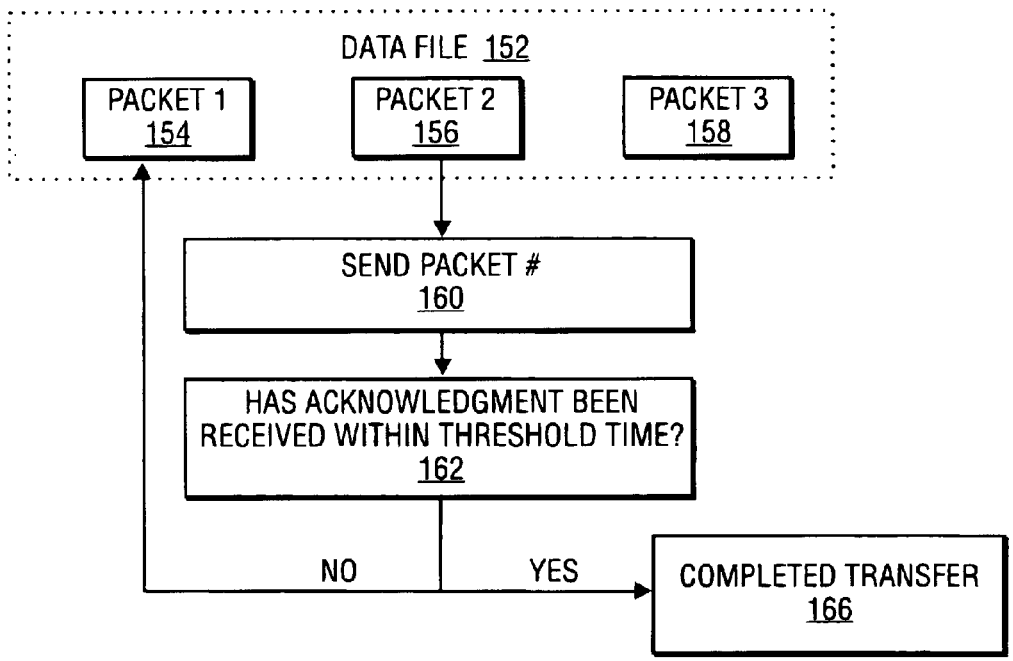

Such an algorithm 150 performed by the acknowledgement unit 48 is shown in FIG. 5 to efficiently send a data file 152 having a first packet 154, second packet 156 and third packet 158. The transmitter sends (step 160) each of the packets comprising the data file 152 for a medical study to the disassembly structure. The transmitter questions (step 162) whether an acknowledgement response has been received for each of the transmitted packets within the threshold period of time. If the acknowledgment is not received, the transmitter considers the entire data file with all packets and identifies (step 164) the lost portion of the data file 150 to which no acknowledgement was received within the threshold period of time. The transmitter resends only those lost portions of the data file 150. If acknowledgment is received within the threshold time, the transmission is considered complete (step 166). In past schemes as shown in FIG. 5B, where an acknowledgement is not received within a threshold time, the transmitter is required to resend all the packets that make up the data file.

Figure 6:
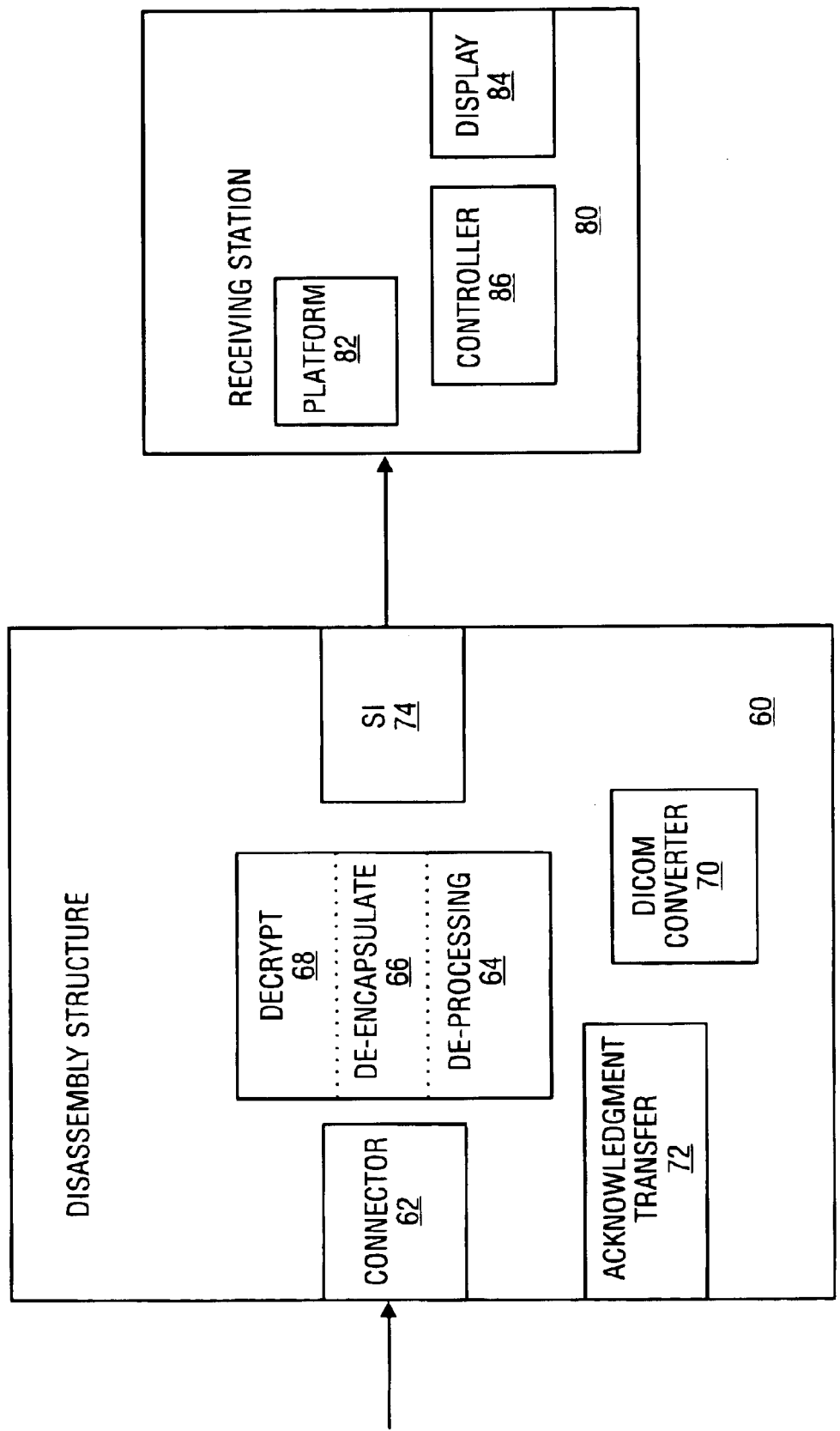
FIG. 6 is a block diagram of one embodiment of a disassembly structure and a receiving station configured in accordance with the teachings presented herein.

Referring once again to FIG. 1, the remote disassembly structure 60 and transmitter 20 may be in communication through a variety of connections. FIG. 6 shows one example of a disassembly structure 60 with a transmitter connector 62 through which the transmitter communicates with the disassembly structure. Typically, transmitter connector 62 is a hypertext transfer protocol (HTTP) connection. The association between the transmitter and disassembly structure is usually a dedicated connection, e.g. public network. The connection may be a telephone line. The communication link may be also made by a serial line Internet protocol (SLIP), point-to-point protocol (PPP), an XDSL link, a satellite or other wireless link, a cable modem, ATM network connection, an ISDN line, a DSL line, or other communication link. ISDN lines and DSL lines are useful because they are digital technologies, thus obviating any need to convert information from digital to analog form prior to transmission.

Where tunnel mode IP security is provided to the packets, the disassembly structure 60 examines the outer IP header and any outer IP extension headers of the received packet and de-processing unit 64 reconstructs the data. The de-encapsulating unit 66 of the de-processing unit 64 strips off the outer IP header. The disassembly structure also may decrypt 68 the packet to reveal the inner packet, such as by using a security parameters index (SPI) in the ESP header.

The IP address, AE title, header or other such identifier of the receiving station is read and the inner packet with medical data is transferred to the appropriate receiving stations 80.

Preferably the inner packet is converted to be compliant with the DICOM Standards (e.g., with IP address, port number and AE title) by dicom converter 70 before being relayed to the receiving stations 80. The dicom converter 70 may convert various types of data to be DICOM compliant, such as video, CT data, twain data, etc. Such conversion software may be conveniently acquired through a plug-in or Activex control.

The disassembly structure 60, through the use of an acknowledgement transfer unit 72 may be configured to send acknowledgments to the transmitter 20 for each data packet that is successfully received by the disassembly structure 60. Thus, the disassembly structure is able read the packet to determine the appropriate transmitter to receive the acknowledgment. The acknowledgment packet is small relative to the medical data packet, e.g., 5–10 bytes.

In another configuration, the disassembly structure 60 includes elements of a transmitter 20, configured to transmit medical data as well as elements to receive medical data from another transmitter. Thus, all of the features of the disassembly structure 60 and transmitter 20 are incorporated into one unit. In still other configurations, the receiving station 80 includes the disassembly structure 60 and is configured to de-process the packets and/or or includes all features of a transmitter 20.

The communication between the disassembly structure 60 and the receiving station 80 takes place through a station interface (SI) 74 of the disassembly structure 60. The communication pathway may be through various mechanisms and usually through a LAN or a WAN. Multiple receiving stations 80 may be connected to receive information from the disassembly structure 20.

Receiving station may be any device configured to receive the data, e.g., a workstation, archive, worklist manager, modality, or DICOM compliant device. In one preferred embodiment, the receiving station 80 may include a platform 82, e.g., a personal computer (PC), such as a Windows™-based PC, Macintosh™, or one of a wide variety of hardware platforms that runs the UNIX™ operating system. The receiving station 80 may further includes a display 84, which is coupled to the platform 82 through a display controller 86. Display 84 may be any one of a number of conventional display devices such as a liquid crystal display or a video display. For sharp colors and grayscale, display 84 is preferably an SVGA monitor, with a resolution of 26 dpi or better, and an active area of at least 17 inches, controlled using a true color video card. High resolution, plain film may be displayed on a Matheus Medical Imaging Board (by Barco Corporation located in Duluth, Ga.) and greyscale display at 2048×2560×8 to 12 bits per pixel. Video display devices that allow for data to be clearly visualized according to the DICOM Standards are contemplated as part of the present invention. In another embodiment, the receiving station 80 is a printer which may be Dicom-compatible and run either a non-proprietary or proprietary operations system (or a conventional Postscript™ printer).

Figure 7:
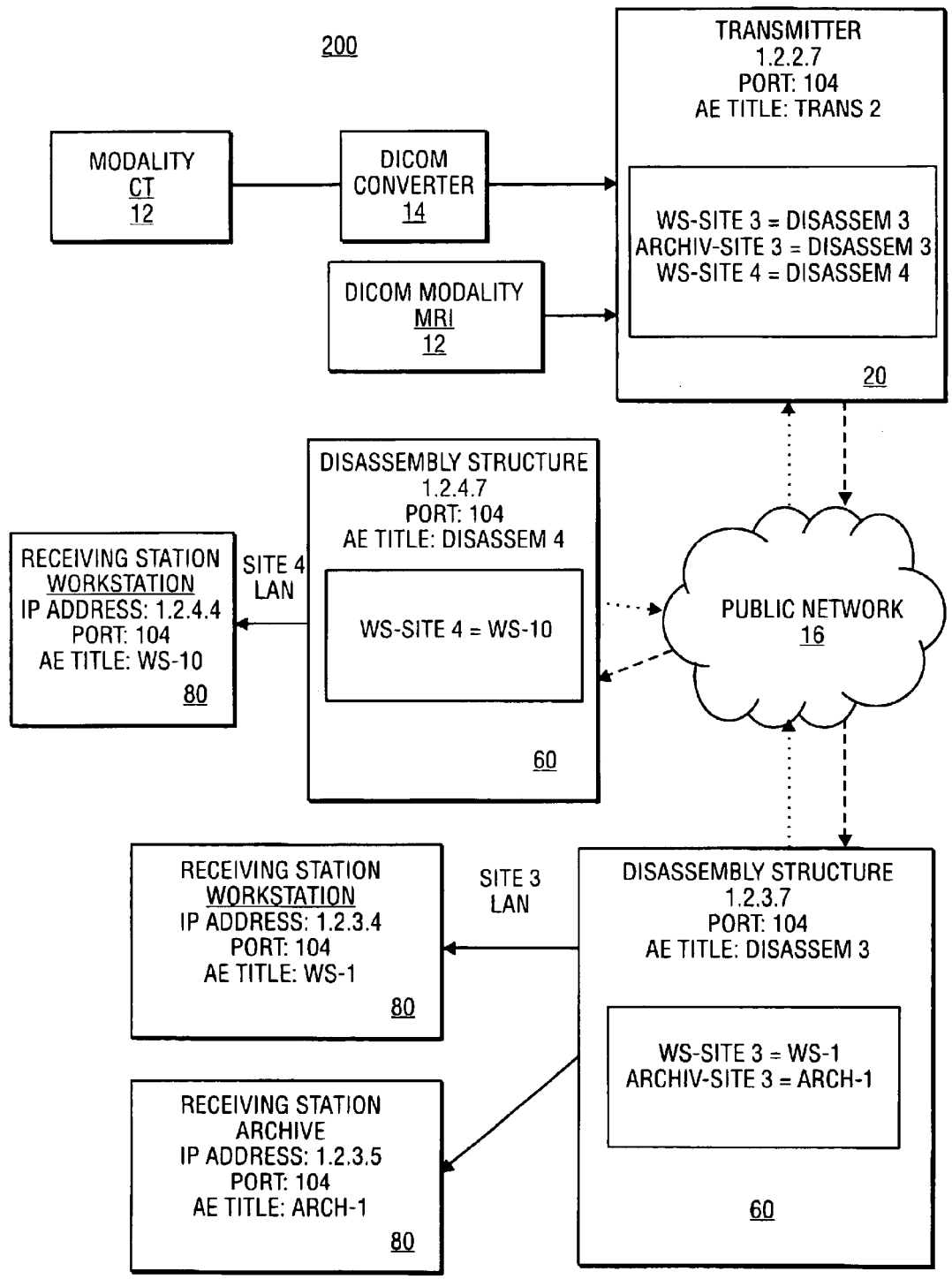
FIG. 7 illustrates one embodiment of a secure network system with multiple sites, modalities and receiving stations any or all of which may be configured in accordance with the teachings presented herein.

Although FIG. 6 shows only one disassembly structure 60 and receiving station 80, in variations of the network system 10, any number of disassembly structures may communicate with the transmitter 20 in the same manner as disassembly structure 60. Preferably the number of disassembly structures is one to several thousand units and more usually about 1 to 100 units. Any number of receiving stations 80 may also be present within a network system. In FIG. 7, another embodiment of a secure network system 200 is shown with two modalities 12 in communication with a transmitter. The transmitter 20 communicates to two sites through separate disassembly structures 60 across a public network 16. Site 3 communicates with a workstation and archive across a LAN and Site 4 communicates with a workstation across a separate LAN.

There are many alternative features that may be added to the secure network system 10 to advance the functionality of the system. Having described the overall system, some optional aspects of the system will now be discussed.

The transmitter 20 may include a firewall inserted between the transmitter and the public network 16 (e.g., the Internet) to establish a controlled link and to erect an outer security wall. All transmitted information must pass through the firewall to reach the disassembly structure 60. The firewall may be a platform for IPSec using tunnel mode capabilities. Thus, a circuit level gateway may be established between the firewall and internal host and between the firewall and outside host.

Preferably, the firewall includes two network ports, e.g. Ethernet ports, in communication with each other. One of the network ports is at the data interface 22 and the other port is at the network interface 50. Thus, data entering through the data interface 22 passes through the first network port and must also pass through the other port to exit the transmitter 20. The firewall may restrict traffic, limit protocols and/or act as a proxy server for some services. The firewall may additionally control direction, users and behavior of services. The firewall may include packet filtering with rules to determine whether to forward or discard and scrutinize applications.

In still other embodiments, the processing unit of the transmitter includes Domain Name System Security (DNSSec). DNSSec is provided to protect the dynamic update operation of DNS. A root name server located on the public network 16, e.g., the Internet, stores the addresses, e.g., source IP addresses, for each disassembly structure 60 or other devices not behind the firewall, on the medical enterprise network as well as associated information needed for the receiving disassembly structure to process the data and relay the data to the appropriate receiving station 80. For example, the root name server receives data packets traveling through the virtual private network and reads the port number of the source transmitter 20. The server cross-references this port number to determine that the data from the transmitter is in the form of IP Security. The server informs the disassembly structure 60 that the data requires IP Security de-processing.

An extension is developed to enable DNS authenticated public key distribution. Through such extensions, the receiving stations 80 may securely obtain autonomous system numbers for the public key mapping. The DNSSec extensions are further described in RFC 2065 by the Internet Engineering Task Force (IETF) and at Web site, www.ietf.org/internet-drafts/draft-ietf-dnssec-secext2-*.txt.

The secret key means of securing DNS transmission is described at Web site, www.ietf.org/internet-drafts/draft-ietf-dnssec-tsig-*.txt. DNSSec updating is described in RFC 2137 by the IETF and at Web site, www.ietf.org/internet-drafts/draft-ietf-dnssec-update2-00.txt.

In still further embodiments, the processing unit 44 of the transmitter 20 may provide for compression of data to conserve storage space and/or provides for the speedy transmission of data to the disassembly structure 60, wherein the disassembly structure 60 may be used to decompress the data. Thus, for one embodiment, the processing unit 44 may use various convenient algorithms that allow data files to shrink in order to compress the data. These algorithms tend to operate by replacing repeating patterns of data with smaller tokens. A header may be added to the data file as it is compressed for conveying information necessary in the reconstruction of the file when it is decompressed. In addition, a header may be included which retains information on the way the data was attained and how one data representation, e.g., an image, relates to another representation in the same set of data, e.g., "series 1, image 39 and echo 2."

Generally, compression formats are either high efficiency or low efficiency and either lossless or lossy. Lossy compression schemes are characterized by components of an original image being absent from a reconstructed image after a compression-decompression cycle. Lossless schemes do not drop any information. Compression levels for any scheme may be chosen to be in compliance with the Food and Drug Administration (FDA) requirements for a particular application, e.g., diagnostics or referral quality.

Low compression schemes (i.e., those that do not provide significant compression ratios) that may be used include joint photographic experts group (JPEG) compression schemes that use Fourier analysis-based methods, such as the discrete cosine transform, to compress data; graphics interchange format (GIF) compression schemes, which use LZW algorithms; bitmapped image compression schemes and tagged image file format (TIFF) compression schemes. Alternatively, high efficiency compression schemes, such as wavelet, motion wavelet, Motion Picture Experts Group (MPEG) motion JPEG, Lempel Ziv and/or fractal compression schemes may be employed. Use of such high efficiency schemes may be preferred where storage space and/or transmission bandwidth is limited. For example, wavelet compression schemes may be 20 times more efficient than JPEG compression schemes, providing for a more detailed representation of the data at the same bit budget.

In one embodiment, a progressive compression scheme is used prior to storage of data, wherein data is incrementally compressed to varying sizes. An advantage of progressive compression is that where the data is prepared for transfer, the transmitter may pull the largest size of data that is capable of being compiled into a package. In this manner, truncation by intermediate hosts causing the loss of data segments is avoided. Moreover, the largest acceptable data size also provides the optimal resolution for the data when it is viewed.

In another embodiment, the processing unit 44 has stored information on the amount of compression and optionally the type of encryption, to be applied for each receiving station. This information may be included in the relational database 28, where the compression and/or encryption information is listed for each station AE title.

In one alternative/optional embodiment, the transmitter 20 is configured to update information regarding new disassembly structures joining the network. An updating unit may attach additional AE titles and their related destinations and IP Addresses (such as alias AE titles) for such new disassembly structures to the relational database 28 and create a distributed database architecture between transmitters 20. The updating unit may receive information by a user manual inputting the new information or by using various known distributed database architecture, such as synchronous asymmetric replication (SAR) and CORBA techniques to update the database with new information. With use of these techniques, the updating unit may manage the distribution of new information across a VPN, WAN, LAN and/or between two or more transmitters 20. The new alias information may be established by and stored in a database in a disassembly structure 60. The disassembly structure 60 preferably notifies all other disassembly structures and transmitters on the network of the existence of the information. The SAR technology may also use complex rules and algorithms to regulate the sequence of data updates and to recover from interruption in communication links between transmitters in a geographically distributed network.

The present invention has been described above in varied detail by reference to particular embodiments and figures. However, these specifics should not be construed as limitations on the scope of the invention, but merely as illustrations of some of the presently preferred embodiments. It is to be further understood that other modifications or substitutions may be made to the described information transfer system as well as methods of its use without departing from the broad scope of the invention. Therefore, the following claims and their legal equivalents should determine the scope of the invention.

What is claimed is:

1. Stored in a computer readable format, computer executable instructions which when executed cause a method to be performed, the method comprising:
   recognizing the identity of a receiving station that is to receive medical data;
   identifying a disassembly structure from the identity of the receiving station; and,
   preparing packets containing the medical data and causing the packets to be sent via a network to the disassembly structure, the preparing comprising attempting to secure the medical data for its transportation over the network by applying to the medical data at least one security technique selected from the group consisting of
   encryption;
   authentication; and,
   key management.

2. The stored computer readable and executable instructions of claim 1 wherein the recognizing comprises recognizing the identity of the receiving station based upon the medical data's content.

3. The stored computer readable and executable instructions of claim 1 wherein the medical data and the identity of the receiving station is to be received by the disassembly structure.

4. The stored computer readable and executable instructions of claim 3 wherein the identity of the receiving station comprises an IP network address.

5. The stored computer readable and executable instructions of claim 4 wherein the IP network address is a private IP network address.

6. The stored computer readable and executable instructions of claim 3 wherein the identity of the receiving station comprises an AE title.

7. The stored computer readable and executable instructions of claim 1 wherein the medical data is in a DICOM compatible format prior to the applying.

8. The stored computer readable and executable instructions of claim 1 wherein the applying further comprises applying an IPSec security technique.

9. The stored computer readable and executable instructions of claim 1 wherein the applying further comprises applying an SSL security technique.

10. The stored computer readable instructions of claim 1 wherein the preparing further comprises preparing between 0.1 megabyte and 5.0 megabyte portions of medical data into each of the packets.

11. The stored computer readable instructions of claim 1 where the method further comprises receiving confirmation of completed packet transfers from the disassembly structure within a threshold time.

12. The stored computer readable instructions of claim 11 wherein the method further comprises causing a resend of those portions of the medical data to which no acknowledgments are received within the threshold time.

13. A method, comprising:
recognizing the identity of a receiving station that is to receive medical data;
identifying a disassembly structure from the identity of the receiving station; and,
preparing packets containing the medical data and causing the packets to be sent via a network to the disassembly structure, the preparing comprising attempting to secure the medical data for its transportation over the network by applying to the medical data at least one security technique selected from the group consisting of
encryption;
authentication; and,
key management.

14. The method of claim 13 wherein the recognizing comprises recognizing the identity of the receiving station based upon the medical data's content.

15. The method of claim 13 wherein the medical data and the identity of the receiving station is received by the disassembly structure.

16. The method of claim 15 wherein the identity of the receiving station comprises an IP network address.

17. The method of claim 16 wherein the IP network address is a private IP network address.

18. The method of claim 15 wherein the identity of the receiving station comprises an AE title.

19. The method of claim 13 wherein the medical data is in a DICOM compatible format prior to the applying.

20. The method of claim 13 wherein the applying further comprises applying an IPSec security technique.

21. The method of claim 13 wherein the applying further comprises applying an SSL security technique.

22. The method of claim 13 wherein the preparing further comprises preparing between 0.1 megabyte and 5.0 megabyte portions of medical data into each of the packets.

23. The method of claim 13 further comprising receiving confirmation of completed packet transfers from the disassembly structure within a threshold time.

24. The method of claim 23 further comprising causing a resend of those portions of the medical data to which no acknowledgments are received within the threshold time.

* * * * *